United States Patent
Archer

(10) Patent No.: US 9,427,593 B2
(45) Date of Patent: Aug. 30, 2016

(54) MEASURING CURRENT DURING DELIVERY OF VOLTAGE REGULATED STIMULATION TO A PATIENT

(71) Applicant: NeuroPace, Inc., Mountain View, CA (US)

(72) Inventor: Stephen T. Archer, Sunnyvale, CA (US)

(73) Assignee: NeuroPace, Inc., Mountain View, CA (US)

(*) Notice: Subject to any disclaimer, the term of this patent is extended or adjusted under 35 U.S.C. 154(b) by 170 days.

(21) Appl. No.: 14/198,259

(22) Filed: Mar. 5, 2014

(65) Prior Publication Data

US 2014/0277288 A1    Sep. 18, 2014

Related U.S. Application Data

(60) Provisional application No. 61/778,246, filed on Mar. 12, 2013.

(51) Int. Cl.
 *A61N 1/36* (2006.01)
 *A61N 1/372* (2006.01)

(52) U.S. Cl.
 CPC ....... *A61N 1/37264* (2013.01); *A61N 1/36153* (2013.01); *A61N 1/37282* (2013.01)

(58) Field of Classification Search
 CPC .................. A61N 1/36157; A61N 1/36153; A61N 1/3706; A61N 1/3708; A61N 1/3937
 See application file for complete search history.

(56) References Cited

U.S. PATENT DOCUMENTS

| | | | | |
|---|---|---|---|---|
| 5,769,873 | A * | 6/1998 | Zadeh | A61N 1/3708 607/29 |
| 6,016,449 | A | 1/2000 | Fischell | |
| 6,299,574 | B1 * | 10/2001 | Ochs | A61N 1/3937 600/7 |
| 6,597,954 | B1 | 7/2003 | Pless | |
| 6,690,974 | B2 | 2/2004 | Archer | |
| 7,174,213 | B2 | 2/2007 | Pless | |

* cited by examiner

*Primary Examiner* — George Evanisko
(74) *Attorney, Agent, or Firm* — Loza & Loza, LLP; David S. Sarisky

(57) ABSTRACT

A system and method for estimating the current delivered to a patient during voltage-regulated electrical stimulation therapy by an implantable medical device includes calculating a total charge delivered and a peak current delivered and the time at which the peak current was delivered using a proxy for the current delivered to the patient and a component such as a current controlled oscillator, the output of which is proportional to the current proxy together with memory for storing values relating to the output proportional to the current proxy. The stored values also may be used to construct a waveform approximating the current delivered to the patient during a therapy of voltage-regulated stimulation. The system and method may be implemented in an active implantable medical device such as an implantable neurostimulator.

17 Claims, 8 Drawing Sheets

MEASURING CURRENT DURING DELIVERY OF VOLTAGE REGULATED STIMULATION TO A PATIENT

CROSS-REFERENCE TO RELATED APPLICATION(S)

This application claims the benefit of U.S. Provisional Application Ser. No. 61/778,246, entitled "Measuring Current During Delivery of Voltage-Regulated Stimulation to a Patient," filed Mar. 12, 2013, which is expressly incorporated by reference herein in its entirety.

BACKGROUND

1. Field

The present technology relates generally to devices, methods and systems for delivering electrical stimulation to a patient, especially delivering stimulation by regulating a voltage.

2. Background

Neurostimulators are known that can be configured to deliver stimulation to a neural target in a patient (e.g., neural tissue) in different ways, such as by regulating voltage, current or charge. When delivering stimulation to a patient using current regulation, the neurostimulator is configured to deliver a constant current to the patient regardless of the impedance of the load (e.g., the neural tissue) into which charge is delivered. When delivering stimulation to a patient using voltage regulation, the neurostimulator is configured to regulate a voltage so that the voltage applied to the load is constant. Thus, as the impedance changes, the current is adjusted to keep the voltage constant. It would useful to monitor the current being delivered to the patient during voltage regulated stimulation and to measure values related to the delivered current.

SUMMARY

The current delivered to a patient during voltage-regulated electrical stimulation therapy by an active implantable medical device, such as an implantable neurostimulator, may be estimated using a proxy for the current delivered to the patient. The current proxy provides values that may be used to calculate one or more of a total charge delivered, a peak current delivered, and the time at which the peak current was delivered.

In one disclosed configuration, an active implantable medical device includes a therapy regulator configured to output an electrical stimulation therapy signal and a proxy signal, the proxy signal being based on the therapy signal. The device also includes circuitry configured to provide a value related to the current delivered to the patient, the value being derived from the proxy signal. The device further includes a processor configured to process the value to determine a measure related to a current delivered to the patient. The proxy signal may be proportionate to the therapy signal, or may be a fraction of the therapy signal.

The circuitry that provides the value may include an oscillator, e.g., a current controlled oscillator, configured to output pulses as a function of current amplitude, and one or both of a phase counter and a peak counter. The phase counter is configured to output as the value a count corresponding to the number of output pulses output by the oscillator over a period of time. The period of time may correspond to one of a plurality of phases of the therapy signal. In this case, the measure derived by the processor may be a total charge that is calculated using the count of output pulses.

The peak counter is configured to monitor for each of a plurality of time windows within one of a plurality of phases of the therapy signal, a count corresponding to the number of output pulses output by the oscillator during the time window. The peak counter is further configured to output as the value the highest count of the plurality of counts. In this case, the measure derived by the processor may be a peak current delivered to the patient that is calculated using the highest count of output pulses.

The processor may be configured to determine the measure every time a therapy signal is output, or periodically as a function of a number of therapy signals output, e.g., every tenth therapy signal, or as a function of time, e.g., once a day. A memory may store the values output by the phase counter and the peak counter. In addition to using the values to derive total charge and peak current, the stored values also may be used to construct a waveform approximating the current delivered to the patient during a therapy of voltage-regulated stimulation.

BRIEF DESCRIPTION OF THE DRAWINGS

The accompanying drawings, which are incorporated in and form a part of this specification, illustrate and serve to explain the principles of embodiments in conjunction with the description. Unless specifically noted, the drawings referred to in this description should be understood as not being drawn to scale.

DETAILED DESCRIPTION

Figure 1:
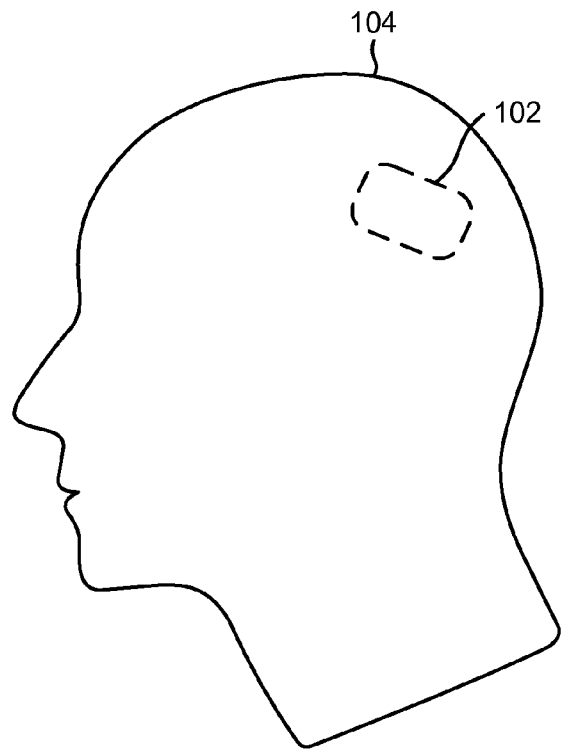
FIG. 1 is a schematic illustration of a patient's head showing the placement of an implantable medical device.

Embodiments enable an implantable neurostimulator to monitor and measure the current delivered to a patient during a therapy of voltage regulated electrical stimulation, such that the results of the monitoring and measuring may be used in various beneficial ways as will be described more fully herein. In some embodiments, a total charge delivered to the patient during the therapy and a peak current delivered to the patient during the therapy are measured based on monitored data. In addition, the measurements acquired according to some embodiments may enable partial or near complete reconstruction of a current waveform that approximates the waveform experienced by the patient while a therapy was delivered.

An active implantable medical device is described which may be configured to deliver programmable stimulation by regulating voltage and to monitor and measure a total charge delivered during at least one phase of a stimulation pulse; to identify at least one peak current during the phase and the time (e.g., corresponding to one of several possible time windows) in which the peak current occurred; and, optionally, to record and store a representation of a current waveform corresponding to delivery of the voltage-regulated stimulation.

Methods are described for monitoring and measuring total charge and peak current delivered by an active implantable medical device as well as methods for acquiring and storing information with which a waveform corresponding to a current delivered by an active implantable medical device during voltage-regulated stimulation may be reconstructed. Also described are systems including an active implantable medical device such as a neurostimulator which are configured to monitor charge and/or current delivered during voltage-regulated stimulation, systems for measuring integrated current (total charge delivered during the stimulation therapy, or during a phase of a pulse of stimulation, as the case may be), as well as systems for monitoring and measuring when the current peaks occur and at what amplitude.

In voltage regulated stimulation, an active implantable medical device is configured to maintain a certain voltage at an output corresponding to a location in a patient's neural tissue (for example, at an electrode positioned in or adjacent neural tissue), while a stimulation therapy is being delivered. In a simple example, if an active implantable medical device configured as a neurostimulator is programmed to deliver a therapy at a voltage of 1 volt, the neurostimulator will monitor the voltage at the output at the neural tissue. If changing impedance of the tissue causes the voltage to vary, the neurostimulator will increase or decrease the current until the voltage drop is regulated back to 1 volt again.

In an active implantable medical device configured to deliver stimulation to a patient's neural tissue through one or more electrodes by regulating a voltage, the user typically is able to program various parameters of therapy. Some of these parameters may define the form the therapy waveform will take. Options may include pulsatile waveforms (e.g., a biphasic charge-balanced square wave, or triangular wave), non-pulsatile waveforms (e.g., a sine wave), or some combination of a pulsatile and non-pulsatile waveform. A pure DC voltage source or close to a pure DC voltage source may also be an option for stimulation in some circumstances.

Other parameters may be available to program the strength or amplitude of a therapy (e.g., in units corresponding to a voltage amplitude or to a current amplitude), the duration of at therapy (e.g., in the case of a pulsatile waveform, the width of a phase), and whether each phase is the same as every other phase or different (e.g., positive phase identical to negative phase, or positive and negative phases different in shape but configured to balance charge). (Positive and negative phases are often used to "charge balance" a neurostimulation therapy, a technique for balancing the charge introduced to the tissue with an equal and opposite charge in the opposite direction. Charge balancing is expected to, among other things, minimize irreversible chemical reactions at the electrode to tissue interface which may change the impedance of the electrodes.)

There are many other parameters of stimulation therapy that may be fixed or programmable depending on a particular configuration of a neurostimulator. For example, the interval between delivery of stimulation waveforms (sometimes referred to as the interpulse interval) may be programmable. If the interpulse interval is very short or zero, then the stimulation will effectively be on continuously.

A stimulation waveform may be delivered as one of two or more similar or different waveforms in a "burst" of therapy, and there may programmable parameters for defining which waveforms comprise a burst and how far apart each burst is to be from another burst. There may also be a parameter for an interval between bursts. Additional insight into the types and kind of parameters that may be programmed for a neurostimulation therapy may be had with reference to U.S. Pat. No. 7,174,213 to Pless et al. for "Electrical Stimulation Strategies to Reduce the Incidence of Seizures" issued Feb. 6, 2007. U.S. Pat. No. 7,174,213 is incorporated herein by reference in the entirety.

It should be appreciated that a given neurostimulator may be provided with the circuitry to, and may be configurable for, delivery of stimulation accomplished using voltage regulation as well as stimulation accomplished in some other way, such stimulation accomplished using current regulation. Since the embodiments described here are concerned with monitoring and measuring currents during voltage regulated stimulation, voltage regulated stimulation is the type of stimulation that will be predominantly discussed.

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure. It should be understood that any aspect of the disclosure disclosed herein may be embodied by one or more elements of a claim.

The concepts disclosed may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a general register, or any other suitable non-transitory medium for storing software.

With reference to FIG. 1, an exemplary active implantable medical device 102 is shown implanted in a patient 104. In one configuration, the implantable medical device 102 includes a small self-contained brainwave detecting device. As the term is used herein, a brainwave detecting or recording device is a device capable of detecting or predicting ictal activity (or other neurological events) for providing data useful in the diagnosis of a neurological disorder. Further, the term recording device, as used herein, is a device that can either record neurological signals, such as EEG signals, or detect and analyze EEG signals and create a log of such an analysis.

The implantable medical device 102 may be configured to detect or predict neurological events that have a representative electrographic signature. For example, the implantable medical device 102 may be responsive to epileptic seizures. It should, however, be recognized that it is also possible to respond to other types of neurological disorders, such as movement disorders (e.g. the tremors characterizing Parkinson's disease), migraine headaches, chronic pain, and neuropsychiatric disorders such as depression.

Figure 2:
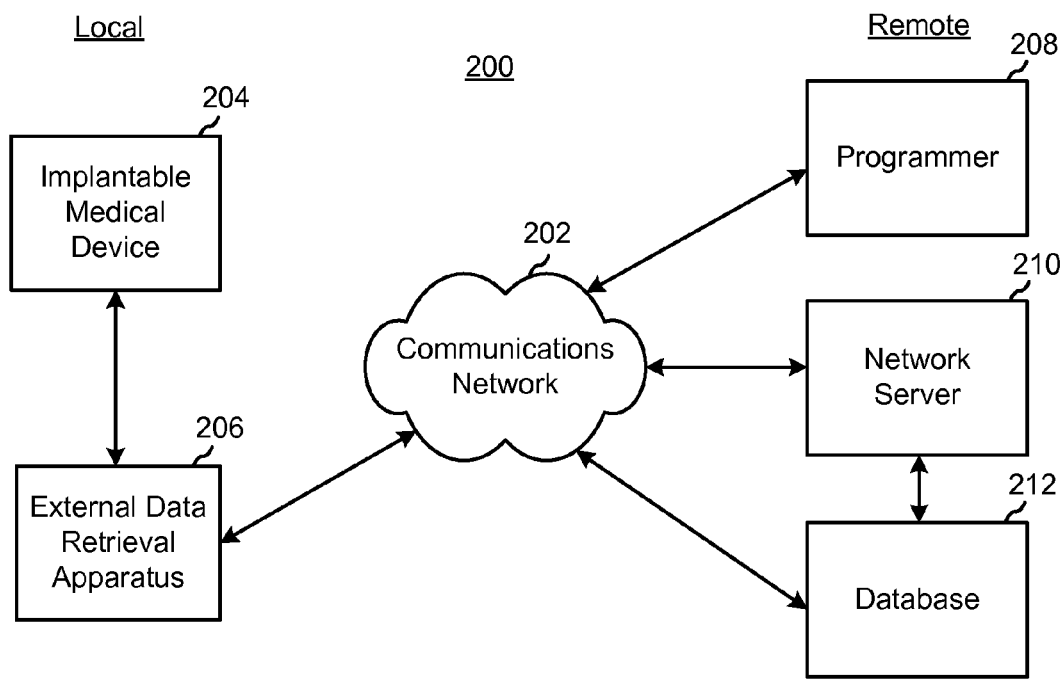
FIG. 2 is a block diagram of a system for providing communication between local medical devices and remote system components.

With reference to FIG. 2, an exemplary patient monitoring system 200 is illustrated. The patient monitoring system 200 includes local components and remote components that communicate through a communications network 202, such as the Internet. Local components are located in the vicinity of the patient, such as the patient's residence, and may include an implantable medical device 204, and a local device 206, referred to herein as a data retrieval apparatus. Remote components are located a significant distance from the patient, such as at a hospital or care provider's office. Remote components may include, for example, a programmer 208, a network server 210 and a database 212.

The programmer 208 is typically operated by medical personnel (such as the patient's treating physician) to control the operation of the implantable medical device 204. In general terms, the programmer 208 functions as a clinical interface to the implantable medical device 204, allowing the implantable medical device parameters to be modified, and for data and/or program code to be uploaded from and downloaded to the implantable medical device.

The database 212 serves as a centralized data repository for all data relevant to the operation of the system 200, and may include clinical data, program code, and more. The network server 210 acts as the primary interface between the database 212 and other devices attached to the communications network 202. Although it might be possible and advantageous in certain circumstances to communicate directly with the database 212, it is generally preferable to configure the network server 210 to receive queries, perform necessary authentication, access the database 212, and respond as necessary, thereby reducing the processing load on the database and also reducing the exposure of the database to network traffic (thereby improving security).

The data retrieval apparatus 206 is configured to receive data from remote components through the communications network 202 and provide it to the implantable medical device 204. Such data may include, for example, program code or instructions from a programmer 208 that affect the operation of the implantable medical device 204. The data retrieval apparatus 206 is also configured to retrieve data from the implantable medical device 204 and to forward it to one or more of the remote components. As described further below, communication between the data retrieval apparatus 202 and the implantable medical device 204 is wireless, and may be in the form of short-range telemetry by inductive coupling or long-range telemetry by RF communications.

Figure 3:
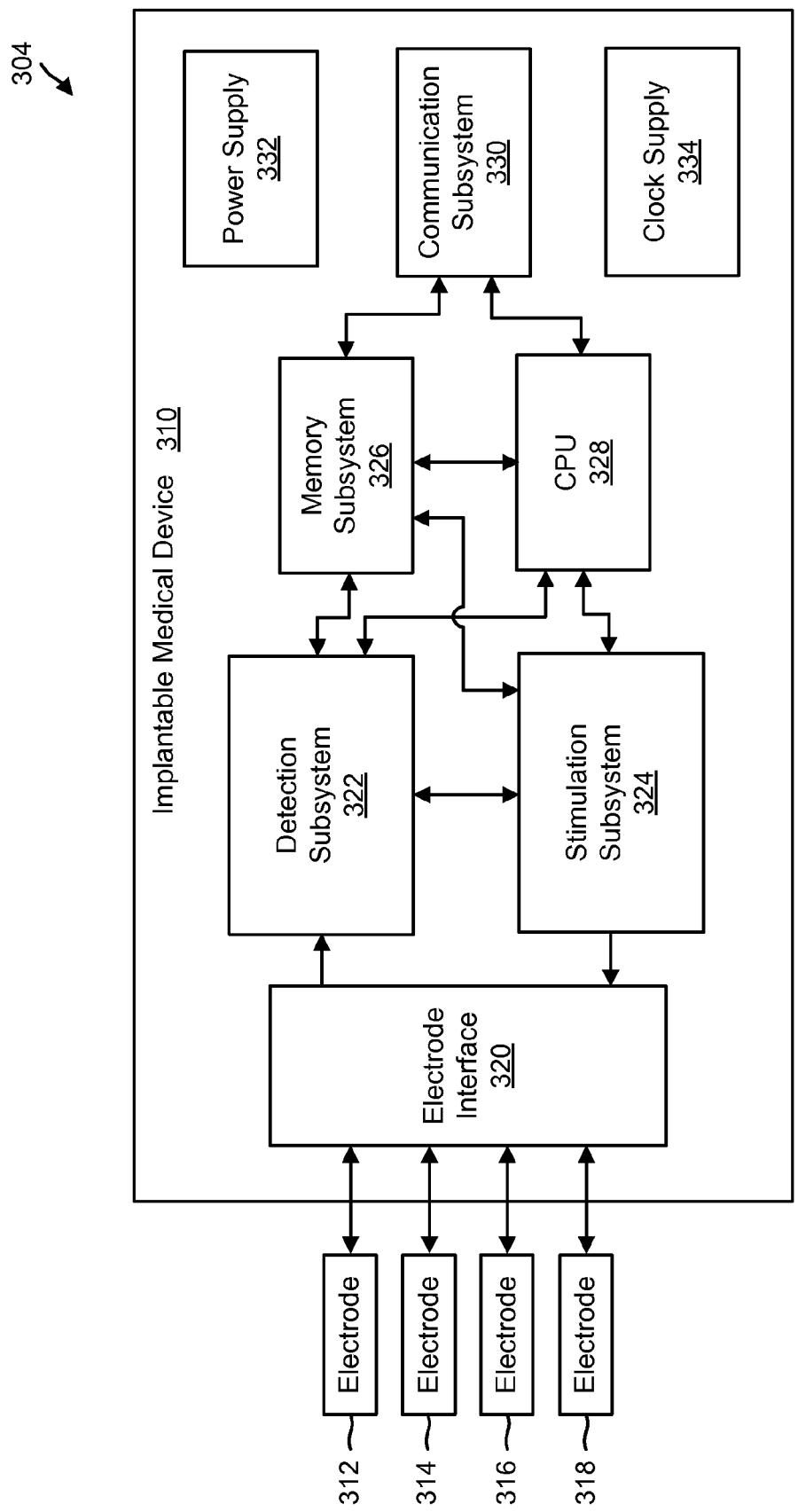
FIG. 3 is a block diagram of an implantable medical device.

An overall block diagram of an implantable medical device 304 used for measurement, detection, and treatment is illustrated in FIG. 3. Inside the housing of the device 304 are several subsystems making up a control module 310. The control module 310 is capable of being coupled to a plurality of electrodes 312, 314, 316, and 318 for sensing and stimulation. Although four electrodes are shown in FIG. 3, it should be recognized that any number is possible.

The electrodes 312-318 are connected to an electrode interface 320. Preferably, the electrode interface is capable of selecting each electrode as required for sensing and stimulation; accordingly the electrode interface is coupled to a detection subsystem 322 and a stimulation subsystem 324. The electrode interface also may provide any other features, capabilities, or aspects, including but not limited to amplification, isolation, and charge-balancing functions, that are required for a proper interface with neurological tissue and not provided by any other subsystem of the implantable medical device 304.

The detection subsystem 322 includes an EEG analyzer function. The EEG analyzer function is adapted to receive EEG signals from the electrodes 312-318, through the electrode interface 320, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., which is hereby incorporated by reference. The detection subsystem may optionally also contain further sensing and detection capabilities, including but not limited to parameters derived from other physiological conditions (such as electrophysiological parameters, temperature, blood pressure, etc.).

The stimulation subsystem 324 is capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 322. As illustrated in FIG. 3, the stimulation subsystem 324 and the EEG analyzer function of the detection subsystem 322 are in communication; this facilitates the ability of stimulation subsystem 324 to provide responsive stimulation as well as an ability of the detection subsystem 322 to blank the amplifiers while stimulation is being performed to minimize stimulation artifacts. It is contemplated that the parameters of the stimulation signal (e.g., frequency, duration, waveform) provided by the stimulation subsystem 324 would be specified by other subsystems in the control module 310.

Also in the control module 310 is a memory subsystem 326 and a central processing unit (CPU) 328, which can take the form of a microcontroller. The memory subsystem 326 is coupled to the detection subsystem 322 (e.g., for receiving and storing data representative of sensed EEG signals and evoked responses), the stimulation subsystem 324 (e.g., for providing stimulation waveform parameters to the stimulation subsystem), and the CPU 328, which can control the operation of the memory subsystem 326. In addition to the memory subsystem 326, the CPU 328 is also connected to the detection subsystem 322 and the stimulation subsystem 324 for direct control of those subsystems.

The memory subsystem 326 may include one or more types of memory, including for example, random access memory (RAM), read only memory (ROM), and non-volatile memory (NVM). As explained further below, within one or more of the types of memory, such as RAM, there may be sections of memory reserved for the following: 1) EEG waveform data (stored ECoG's), 2) detailed event data regarding detection activity, 3) long-term histogram data on detections, and 4) device diagnostic information (battery voltage, lead impedance, radio usage, etc)

Also provided in the control module 310, and coupled to the memory subsystem 326 and the CPU 328, is a communication subsystem 330. The communication subsystem 330 enables communication between the implantable medical device 204 (FIG. 2) and the outside world, e.g., the data retrieval apparatus 206 (FIG. 2). The communication subsystem 330 may include a telemetry coil (which may be situated outside of the housing) enabling short-range transmission and reception of signals, to or from the implantable medical device 204, via inductive coupling. The communication subsystem 330 may also include a transceiver and one or more antennas for long-range telemetry by an RF communications link with the implantable medical device 204.

Rounding out the subsystems in the control module 310 are a power supply 332 and a clock supply 334. The power supply 332 supplies the voltages and currents necessary for each of the other subsystems. The clock supply 334 supplies substantially all of the other subsystems with any clock and timing signals necessary for their operation.

While the memory subsystem 326 is illustrated in FIG. 3 as a separate functional subsystem, the other subsystems may also require various amounts of memory to perform the functions described above and others. Furthermore, while the control module 310 is preferably a single physical unit contained within a single physical enclosure, namely the housing, it may comprise a plurality of spatially separate units each performing a subset of the capabilities described above. Also, the various functions and capabilities of the subsystems described above may be performed by electronic hardware, computer software (or firmware), or a combination thereof.

Figure 4A:
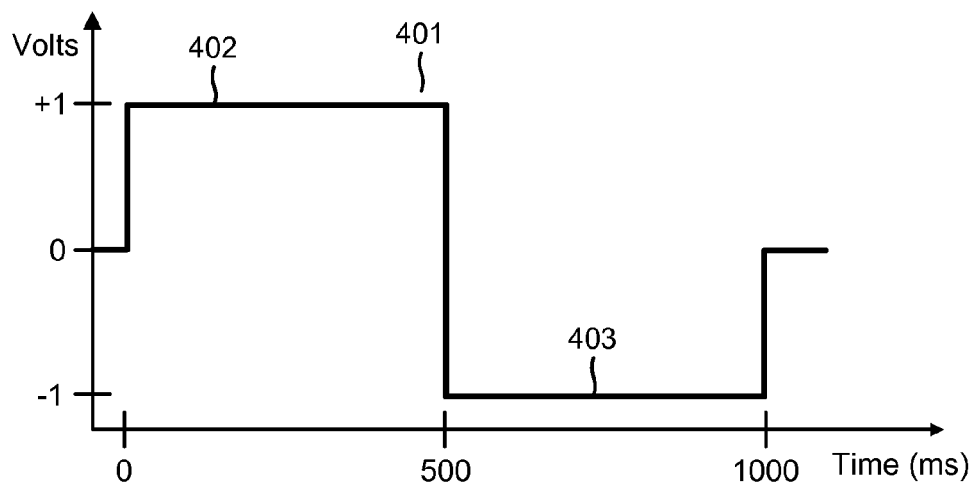
FIG. 4A is a graphical representation of a pulse comprising a one-volt, biphasic square wave of 500 ms per phase which may be delivered to a patient in accordance with embodiments.

Referring now to FIG. 4A, a biphasic square wave pulse 401 characterized by a positive phase 402 that is the same as a negative phase 403 is shown. Such a pulse 401 may be used with embodiments as a stimulation therapy for a patient. A therapy may comprise delivering just one pulse 401, or it may comprise delivering a series of pulses 401 one after the other with a relatively short or a relatively long interval in between each pulse. In still other therapies, the 1 volt square wave pulse may be combined with one or more other of the same or different waveforms to comprise a burst of therapy, the neurostimulator may be configured to deliver one or more bursts of therapy under certain conditions (e.g., periodically or in response to some sensed condition or detected neurological event).

In FIG. 4A, the pulse 401 is characterized by two equal phases centered around zero volts. This configuration may be selected to encourage charge balancing at the electrode-to-tissue interface (i.e., so that the amount of charge delivered to the patient in the first, positive phase 402, is balanced by the charge pulled back during the second, negative phase 403). As will be described below, the extent to which charge is actually balanced may be assessed in a system according to embodiments in which the total charge per phase of a stimulation pulse may be monitored and measured.

The amplitude of the pulse 401 is about 1 V, and the width of each phase 402, 403 is 500 ms. It will be appreciated that a phase width of 500 ms constitutes a relatively long pulse insofar as the voltage will be applied for about half a second in each phase. This may be contrasted to much shorter pulse widths that may be used in electrical stimulation therapies, such as therapies in which pulse widths on the order of 50 to 500 μs are used in one or a burst of pulses. Stimulation pulse widths on the order of 50 to 500 μs used in stimulation therapies are described in U.S. Pat. No. 6,690,974 to Archer et al. for "Stimulation Signal Generator for An Implantable Device" issued Feb. 10, 2004. U.S. Pat. No. 6,690,974 is incorporated herein by reference in the entirety.

It will be appreciated that if a neurostimulator is programmed to deliver pulses such as the pulse 401 in a series with a relatively short interpulse interval or even an interpulse interval of zero time, so that the pulses follow one right after the other, with little or no break between pulses, then the stimulation effectively would be delivered continuously to the patient. If the pulses are delivered further apart, the stimulation would be on for a relatively long time with a resting period in between.

According to Ohm's Law, the amount of current delivered to a patient during application of a voltage across neural tissue will depend on the amplitude (voltage) and the impedance that characterizes the pathway or pathways across which the voltage is imposed. Such a pathway could be from an electrode on the end of a brain lead back to a conductive housing of the neurostimulator or between two different electrodes located on a brain lead or brain leads. Configurations of electrodes used with neurostimulators (both in delivering stimulation to and sensing information from a patient's brain) are described in U.S. Pat. No. 6,597,954 to Pless et al. for "System and Method for Controlling Epileptic Seizures with Spatially Separated Detection and Stimulation Electrodes" issued Jul. 22, 2003, and U.S. Pat. No. 6,690,974 to Archer et al. for "Stimulation Signal Generator for An Implantable Device" issued Feb. 10, 2004. U.S. Pat. No. 6,597,954 is also incorporated herein by reference in the entirety.

It will be appreciated that when as the impedance varies, the voltage at the electrode (or at the neurostimulator therapy output) will change, and the neurostimulator will regulate the voltage so that it is maintained at some predetermined value (e.g., a value that is established at the factory or by programming the neurostimulator after it has been implanted, such as with an external component commonly referred to as a "programmer"). Programmers are described, inter alia, in U.S. Pat. No. 6,597,954.

For example, if the pulse of FIG. 4A is a programmed therapy voltage pulse, then a neurostimulator (such as a therapy stage of a neurostimulator) will regulate the output voltage so that about +1 volt is maintained across the patient for half a second (see the positive phase 402 of the pulse 401 of FIG. 4A) followed by −1 volt for the next half second (see the negative phase 403 of the pulse 101 of FIG. 4A).

Figure 5:
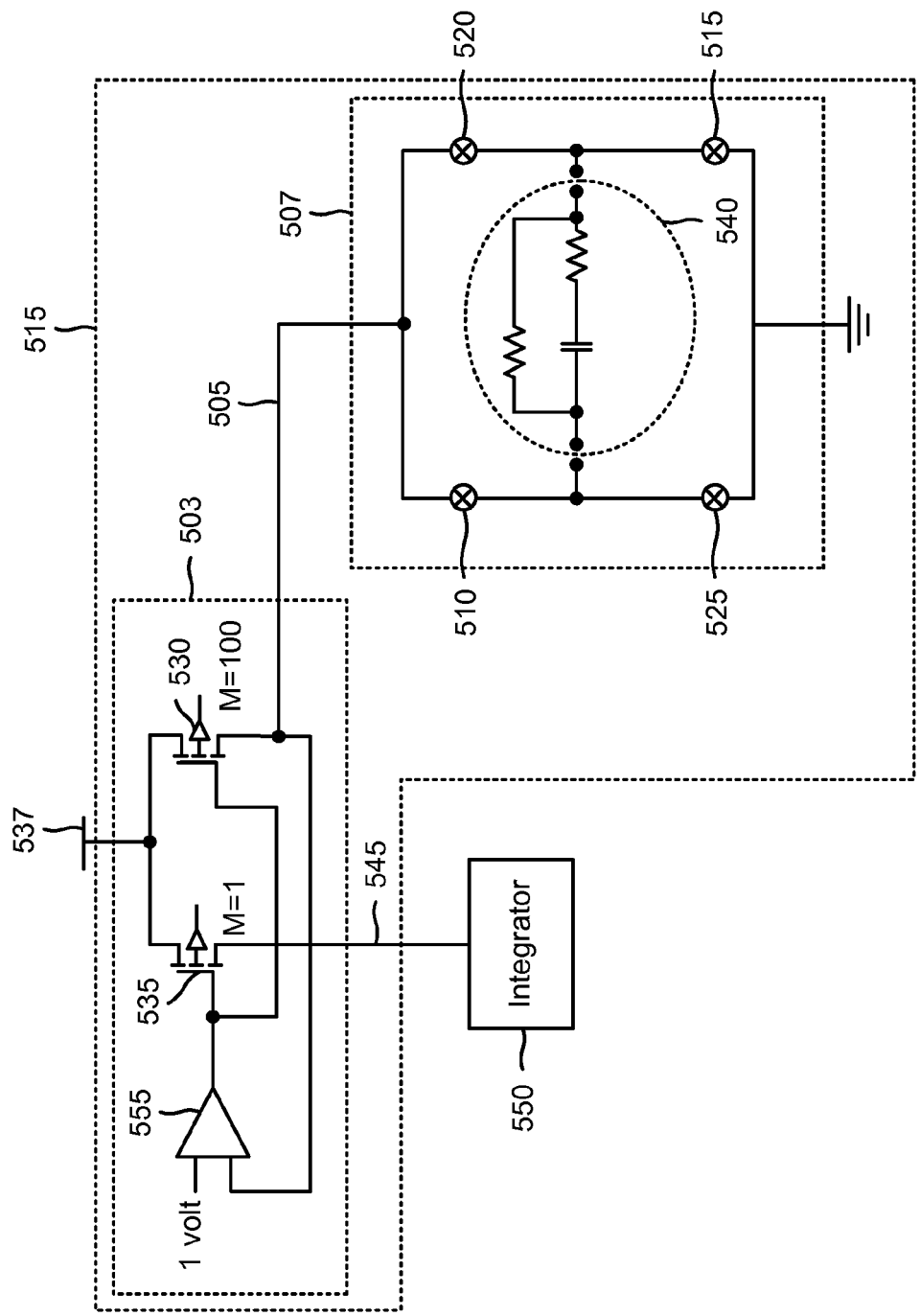
FIG. 5 illustrates a schematic diagram of a circuit that includes elements for monitoring the current delivered to a patient during voltage regulated stimulation according to embodiments.

Referring now to FIG. 5, a first output 505 of a therapy regulator 503 serves as an output of a therapy stage 507 of an implantable neurostimulator can be delivered to a patient. The output 505 is delivered by manipulating (opening and closing) the switches 510, 515 or the switches 520, 525. The patient is represented by the electrical model 540 in FIG. 5 of a therapy stage 507. In the example where the stimulation pulse is a 1 volt square wave, the voltage would be regulated to maintain the output 505 at ±1 volt for the duration of the 1 second pulse. A voltage amplifier circuit such as an operational amplifier 555 is shown configured to control the gates of first p-FET 530 and a second p-FET 535 such that the output 505 is maintained at 1 volt.

Figure 4B:
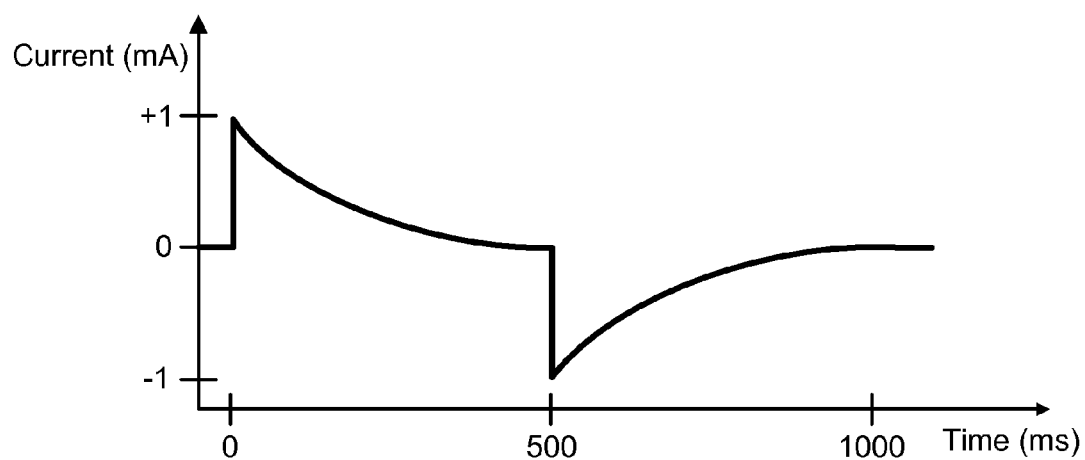
FIG. 4B is a graphical representation of a waveform that may correspond to the current flowing through the patient when the pulse of FIG. 4A is delivered.

FIG. 4B is an example of a waveform that might correspond to the current delivered to the patient during each of the two phases 402, 403 of the stimulation pulse 401. The amplitude of the current (which may be measured in units that correspond to mA) will peak near the beginning of each 500 ms phase, and then decay approximately exponentially until the next phase. (The waveform of FIG. 4B is merely an example to illustrate embodiment described here; the actual current waveform associated with a given iteration of a stimulation pulse corresponding to the biphasic square wave pulse 401 will obviously depend on the impedance of the actual tissue on which the voltage pulse is imposed.)

Referring again to FIG. 5, measuring the total charge delivered during a pulse of voltage-controlled stimulation as well as measuring a peak current or currents and the time(s) at which each peak occurs will be described. Therapy stage 507 of a neurostimulator may be connected in and out of the patient 540 via either a first switch pair 510, 515 or a second switch pair 520, 525 (depending on the polarity of the stimulation pulse phase). When commanded to deliver a stimulation therapy, the therapy stage 507 produces at least two outputs. The first output is a therapy output 505. When a circuit including the therapy output 505 and the patient 540 is completed (e.g., by opening the switches 501, 515 or the switches 520, 525), current will flow through the patient based on the voltage at the therapy output 505. During delivery of a given therapy, the neurostimulator will regulate the voltage (e.g., by drawing more or less current from the neurostimulator power supply 537) to maintain the voltage at which the therapy is intended to be characterized (e.g., at the programmed voltage amplitude).

During delivery of a therapy, a proxy for the current flowing through the patient is created. This current proxy is a second output 545 of the therapy regulator 503. In FIG. 5, the current proxy 545 is obtained using a current mirror for the transistor or transistors that generate the therapy output 505. In one embodiment, the current proxy 545 may represent about $1/100^{th}$ of the current flowing through the patient by reason of the voltage present at the therapy output 505. The portion of the electrical stimulation therapy signal 505 to select for the purpose of tracking or following the current being delivered through the patient may be the lowest portion practical based on considerations of system noise and the required precision of the current measurement. Generally, using a higher ratio of current for the proxy 545 will result in a more accurate measurement of the stimulation current 505 at the expense of battery consumption. The fraction of the electrical stimulation therapy signal 505 that is mirrored may correspond to a fixed value or may be a programmable parameter of the implantable neurostimulator.

In the embodiment of FIG. 5, a first p-FET 530 allows current to flow from the source to the drain when a gate voltage is applied. Thus, when the patient is connected into the circuit by operation of the switch pair 510, 515 or the switch pair 520, 525, the current flowing through the first p-FET 530 will correspond to the current flowing through the patient at the programmed (or otherwise specified) voltage. The second p-FET 535 is configured to have the its gate shorted to the gate of p-FET 530, so that the second p-FET 535 will be supplied with the same gate-to-source voltage. The second p-FET 535 will be controlled with the same gate to source voltage as is applied to the first p-FET 530. Thus, as long as the power supply 537 is high enough to keep both of the first and second p-FETs 530, 535 in saturation, the current waveform corresponding to the current that passes from the drain to the source when the first p-FET 530 is turned on at a given voltage will be substantially identical to the current waveform associated with the second p-FET 535.

Desirably, the characteristics of the first p-FET 530 and the second p-FET 535 are well matched in terms of their properties (e.g., channel length, width, threshold voltage, etc.) so that the current waveform corresponding to the output of the second p-FET 535 will accurately track the output of the first p-FET 530.

In some embodiments, and as alluded to above, the current proxy or mirrored signal will correspond to only a fraction of the output of the first p-FET 530. For example, 100 p-FETs 530 may be used to produce the therapy output 505 whereas only a single p-FET 535 may be used to produce the current proxy 545. This circumstance is reflected in FIG. 5 by the "M=100" designation for the first p-FET 530 and the "M=1" designation for the second p-FET 535. In this configuration, the current proxy signal 545 will track the therapy output 505 but will only represent about $1/100^{th}$ of the current being delivered to the patient.

The current proxy 545 is introduced to an integrator circuit 550, which is described in more detail with reference to FIG. 6. Generally, the integrator circuit 550 allows the current flowing through the patient to be monitored at various times and for various purposes, including for the purpose of measuring the total charge delivered to the patient during all or just a portion of a therapy and for the purpose of measuring the peak current the patient experienced during all or a portion of a therapy.

Depending on the circumstances under which a neurostimulation system is configured to generate and deliver stimulation therapies by voltage regulation, measuring the total charge and/or peak current(s) may be accomplished every time a therapy is delivered for the entirety of the therapy (e.g., over a complete pulse). Alternatively, measuring the total charge and/or peak current(s) may be accomplished only periodically, such as every $10^{th}$ time a therapy is delivered, or once a week regardless of how many times a therapy has been delivered in the previous week, and so on and so forth. Current measurements may be made with a frequency relevant to, for example, how often stimulation therapy is delivered. For example, in a system in which a neurostimulator is configured to deliver stimulation in response to a signal sensed or monitored from the patient (e.g., "responsive stimulation"), current may be measured for every phase of every stimulation therapy delivered or only once per day, or based on some other criteria. The frequency with which measurements are acquired may be related to an intended use of the collected information. For example, if the system is used to enforce a strict limit on the peak current that may be delivered to a patient during any one phase of voltage-regulated stimulation, then every phase may be required be measured and compared to a predetermined threshold. If a measurement indicates that a threshold has been exceeded, then a system may be configured to automatically reduce the stimulation voltage to avoid exceeding the threshold again. By way of another example, one important use for the measured current data may be to conserve the battery. In this case, measuring current data only once a day or even once a week may be sufficient to keep track of the rate of the implant's battery depletion.

Figure 6:
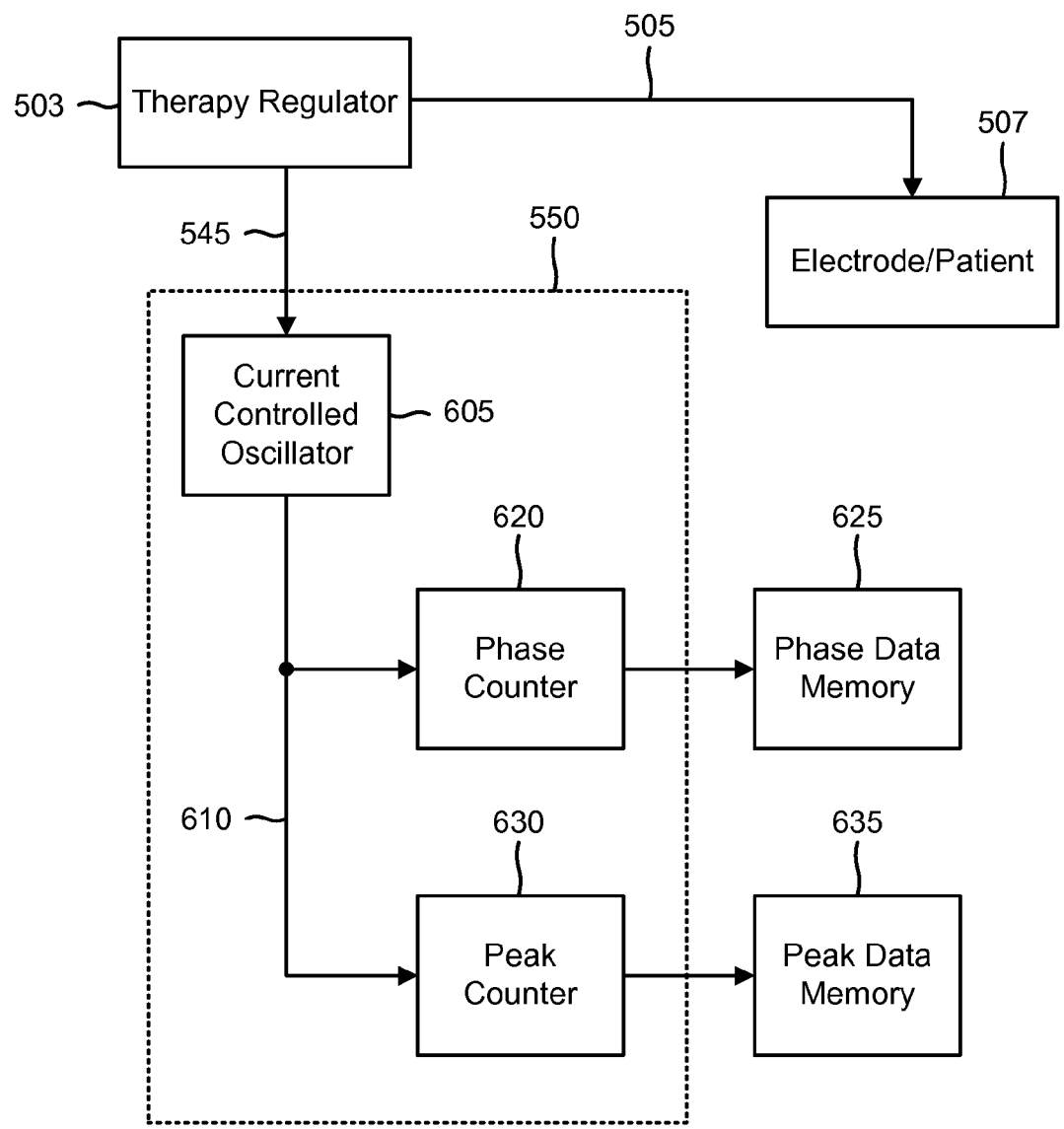
FIG. 6 illustrates a schematic diagram of a circuit that includes elements for measuring and storing aspects of a current waveform corresponding to the current delivered to a patient during voltage regulated stimulation.

In some embodiments, and with reference now to FIG. 6, the current proxy signal 545 is provided as an input to a current controlled oscillator 605. A current controlled oscillator is a circuit configuration that includes an oscillator that oscillates at a frequency that is a function of the input current. The current controlled oscillator may generate logic pulses at a rate corresponding to the frequency of oscillation such that when the current increases, more logic pulses are output from the current controlled oscillator and when the current decreases, fewer logic pulses are generated. In some embodiments, the logic pulses could comprise voltage pulses. In other embodiments, the logic pulses could comprise current pulses or flashes of a light-emitting diode (LED) or some other pulse realizable using components for generating signals to be used in digital logic.

Figure 7:
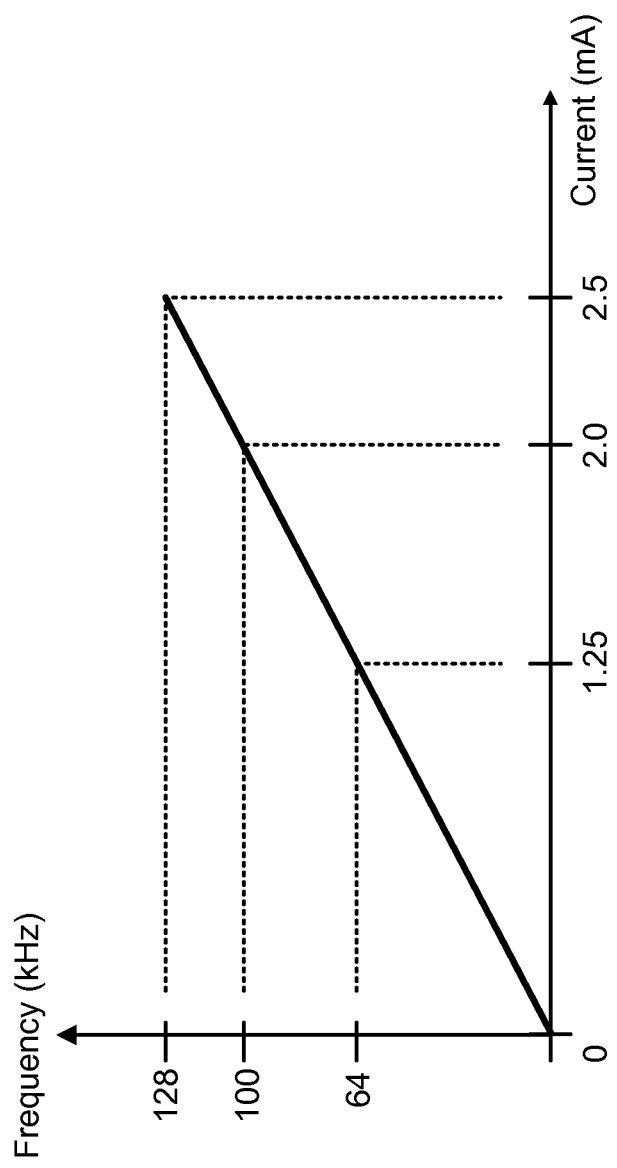
FIG. 7 is a graph illustrating the proportional relationship of current to the frequency at which a current controlled oscillator oscillates that may be used in a circuit such as the circuit shown in FIG. 6.

The relationship of the input current 545 to the output frequency 610 for a current controlled oscillator 605 may be linear, as shown in FIG. 7. In FIG. 7, when the input to the current controlled oscillator is about 2.5 mA, the frequency of the oscillator is 128 KHz. In this case, the current controlled oscillator may output logic pulses at a rate of 128 KHz whenever the current is at 2.5 mA: The frequency of the output 610 may be higher for higher amplitude currents and lower for lower amplitude currents. When the input to the current controlled oscillator 605 is the current proxy signal 545, the frequency at which the oscillator oscillates can be monitored over the course of delivery of the therapy and generated logic pulses used to measure aspects of the current delivered to the patient as is described in more detail below.

For example, a counter such as the phase counter 620 can be configured to count all of the logic pulses generated by the current controlled oscillator 605 during delivery of the positive phase 402 of the pulse 401 of FIG. 4A. The sum of the logic pulses will corresponds to the total amount of current delivered to the patient over the phase width of 500 ms. In an example, if the total number of logic pulses output by the current controlled oscillator is 20000 (twenty thousand) for a 500 ms phase of a 1 volt square wave therapy pulse, then the total charge delivered to the patient for that phase may be computed as follows: Use the linear relationship shown in FIG. 4 to convert the accumulated counts from the phase counter 620 to average current measured in amperes for the phase. The relationship inferred by FIG. 7 is that an input of 2.5 mA results in an output of 128 kHz or 51.2 kHz output per 1 mA input. Dividing the number of counts (20000 in this case) by the duration of the phase (0.5 seconds in this case) results in an average oscillator frequency during the phase was 40 kHz. Subsequently dividing the 40 kHz output seen in the example by the 51.2 kHz per mA yields the result that the average current flow during the phase was 0.781 mA. This result (0.781 mA in this example) may be multiplied by the time period (500 ms in this example) to yield that the total charge delivered during this phase 402 was 390.5 micro-coulombs.

Thus, the information monitored by the phase counter 620 can be used to derive the total amount of charge delivered to the patient over the positive phase 402. It will be appreciated that an average charge delivered during the positive phase 402 may be calculated by multiplying the average current during the phase by the length of the phase (e.g., 500 ms). A measurement of the total charge delivered during a stimulation therapy may be used in a calculation to estimate the rate at which a power supply is being drained (e.g., how much of a battery's capacity is being used). Such a calculation may be performed by the active implantable neurostimulator with the implant's power supply. Alternatively, the calculation may be performed off-line, by an external component or computer, using data concerning the total charge delivered that is transferred from the implant. When the stimulation therapy is a biphasic pulsatile form of therapy, a measurement of the total charge in one phase also may be compared to the total charge of a phase that had opposite polarity. Such a comparison would yield an estimate of how well the two phases are charge balanced, where the objective may be that the net charge delivered be close to or equal to zero.

Additionally, a counter such as the peak counter 630 shown in FIG. 6 can be configured to count the logic pulses 610 output from the current controlled oscillator 605 in each of a plurality of discrete time windows during delivery of a phase of stimulation. The resolution of these time windows may be a programmable variable. For a phase width of 500 ms, each time window may be 2 ms. The peak counter 630 may keep track of the number of logic pulses output from the current controlled oscillator in 2 ms windows during the 500 ms-long phase. Determining the 2 ms window in which the peak current occurred may be accomplished by comparing the number of logic pulses counted in a given 2 ms window to the number of logic pulses counted in a previous 2 ms window (or to a reference number of logic pulses if the window in the first time window for a phase) until the 2 ms with the highest number of logic pulses is identified. The number of logic pulses in that window will be proportional to the peak current (e.g., 200 pulses/2 ms=100,000 pulses/sec or 100 KHz), which may correspond to a current of 2 mA). It will be appreciated by one with ordinary skill in the art that this invention measures the average current during each 2 ms window. The 2 ms windows are sufficiently short that the average current during such a window is measure of the peak current with a 2 ms time resolution.

Accordingly, by sampling the current controlled oscillator output 610 in time windows of uniform size throughout delivery of a therapy (e.g., an entire pulse or one phase of a pulse of stimulation or during a sine wave of stimulation therapy), the output 610 can also be used to determine when during delivery of the therapy the patient experienced a peak current (or peak currents), and the value to which each occurrence of a peak current corresponds (e.g., a number of amplitude units corresponding to the peak may translate into mA of current). (When a stimulation therapy is pulsatile and has a relatively simple morphology, such as the biphasic square wave of FIG. 4A, then there likely will only be one peak per phase, but it will be appreciated that for different pulse morphologies, a given phase may be characterized by more than one peak current as it is delivered to the patient).

In other embodiments, the peak counter 630 may be configured to count logic pulses 610 in each of a sequence of time windows early on during a phase (or whenever the peak or peaks are expected to most likely occur) rather than over the entire phase. In still other embodiments, the time windows into which a phase of a pulse is divided may not be of equal length, provided the system is provided with a way of normalizing the number of logic pulse counts for each time window so that the data is still relevant to identifying a peak or peaks.

Data from each of the phase counter 620 and the peak counter 630 may be stored in memory for later use by an active implantable medical device according to embodiments. Although a phase data memory 625 and a peak data memory 635 are shown in FIG. 6, it will be appreciated that these functional distinctions need not be made in a real world implementation of an embodiment: data relating to the total charge delivered during all or a portion of a given therapy and the peak current or peak currents delivered to the patient during the therapy may be stored in any portion of an active implantable medical device's memory.

In some embodiments, the number of logic pulses measured in each of the time windows during a therapy or during part of a therapy (e.g., during a first positive phase of a therapy) may be retained (e.g., stored in memory) and later read out to reconstruct a waveform corresponding to the current delivered to the patient during the therapy. Referring again to FIGS. 4A and 4B, if the therapy delivered was the 1 volt biphasic square wave of FIG. 4A, and information corresponding to the amplitude of the current during consecutive 2 ms windows over the course of delivery of each phase was acquired for the phase (e.g., by keeping track of the number of logic pulses output by the current controlled oscillator 605 in each of the 250 two ms time windows), and that data was stored, the data might result in a reconstruction of the current waveform that looks something like the current waveform shown in FIG. 4B. The peak current delivered to the patient occurs at the beginning of the positive phase 402 and then tapers off exponentially, and when the negative phase 403 begins, the peak current (albeit with the opposite polarity) occurs again, and then the current tapers off exponentially as the negative phase is completed. In FIG. 4B, the peak currents appear to occur at about 1 mA in the first 2 ms window of the positive phase 402, and at about −1 mA in the first 2 ms window of the negative phase 403. (Again, the waveform of FIG. 4B is only an example, an actual waveform corresponding to the current delivered to a patient may look quite different from FIG. 4B, depending on the impedance of the electrode(s) used and the patient's tissue. For example, the current during the second phase 403 may be expected to have a higher peak value the peak current of the first phase. In some embodiments, it is assumed that the capacitor of the patient model 540 gets charged to approximately 1 volt during the first phase 402. This 1 volt will oppose current flow through the patient towards the end of this first phase. At the start of the second phase 403 this one volt will be reversed and therefore will contribute to the voltage across the patient and will increase the current flow. Thus, the peak current at the start of the second phase 403 may have a greater magnitude than the peak of the first phase 402.

In other embodiments, a peak counter such as the peak counter 630 may be configured to count the logic pulses 610 every 2 ms for the first 26 ms of a 500 ms pulse phase (for example, if that 26 ms is where the peak current would be expected to occur), and that information is stored in memory, then the information later may be retrieved and used by a system to partially reconstruct a waveform corresponding to the current that was delivered to the patient during that 500 ms pulse phase. (A system may be configured to guess or predict what the rest of the current waveform looks like based on known factors other than current data monitored and stored during delivery of a therapy.) In still another example, a counter such as the peak counter 630 may be configured to have greater resolution at the beginning of a therapy (e.g., count ever 2 ms for the first 100 ms of a positive phase of a square wave pulse) than at the end of a therapy (e.g., count every 100 ms for the last 400 ms of a phase), the information may be stored and then later used to approximate the current delivered to the patient during that phase.

It will be appreciated that each of the phase counter 620 and the peak counter 630 should be appropriately sized so that a counter does not overflow before data for a given measurement can be fully acquired. However, each counter also needs to be able to run fast enough to provide the desired resolution for each measurement. In some embodiments, counters with 10-bit width may be appropriate. In other embodiments, counters with a different n-width may be indicated.

Figure 8:
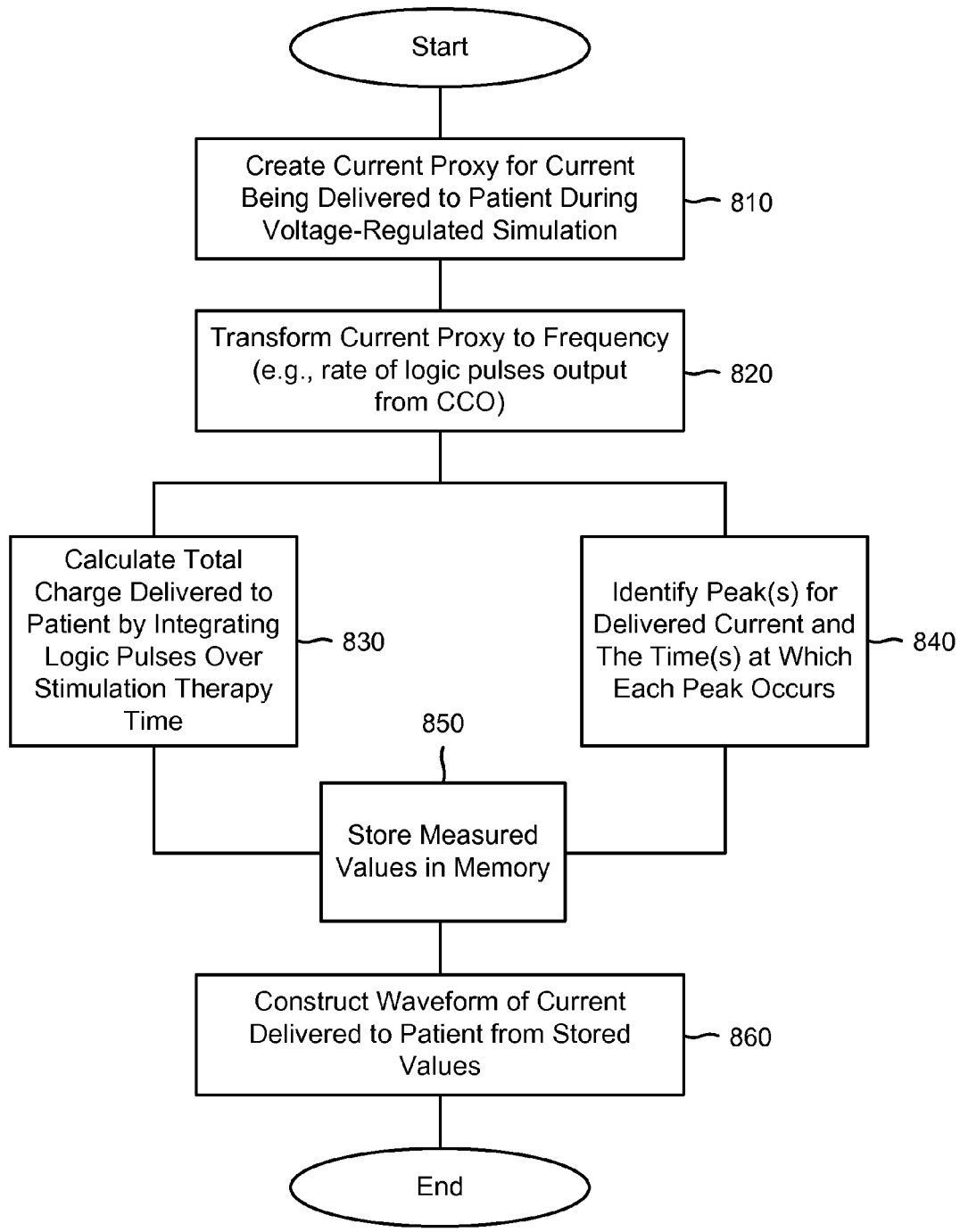
FIG. 8 is a flow diagram of a method for monitoring and measuring current during delivery of voltage regulated stimulation according to embodiments.

Referring now to FIG. 8, in a method of measuring a total charge delivered to a patient during a therapy according to embodiments, a current proxy 545 corresponding to the current being delivered to a patient is created at block 810. At block 820, the current proxy 545 is transformed into a frequency 610 (for example, e.g., a rate of logic pulses output from a current controlled oscillator). The frequency 610 may be monitored over the course of delivery of a therapy (e.g., during the 500 ms positive phase 402 of the 1 volt square wave pulse 401 of FIG. 4A). From this frequency data, at block 830, a total charge delivered to the patient may be calculated (e.g., as the sum of the logic pulses output from the current controlled oscillator over the entire phase width (i.e., 500 ms). The data used to calculate the total charge delivered preferably is stored in a memory block 850.

Referring now to block 840, the frequency 610 also may be monitored at discrete intervals during delivery of the therapy (e.g., during consecutive 2 ms time windows comprising the 500 ms phase width). In each 2 ms window, the peak counter 630 counts the number of logical pulses 610 output from the current controlled oscillator 605 and compares that number to a previous value. Whenever the number of pulses counted in a given window is higher than the number of pulses counted in a previous window, the higher number of pulses is used as the benchmark to which the number of pulses in the next window is compared.

After the counts for all of the 2 ms windows from the period of interest (where a period of interest could be an entire pulse, a phase, or a portion of a phase) have been acquired, the window that exhibited the highest number of counts for that period of interest is determined to represent the peak value for that period of interest. A current amplitude value to associate with each peak then may be calculated based on the known proportionate relationship of the current and the frequency. The particular window(s) in which the highest number of counts was/were obtained will relate to when (with 2 ms resolution) during delivery of the phase the current reached the peak value(s). The data corresponding to each peak current value and the time window in which each peak current value occurred preferably are stored in a memory at block 850.

Once a period of interest is over, the peak counter may be reset or initialized so that it can count the logic pulses output from the current controlled oscillator 605 during the windows corresponding to the next period of interest of the therapy signal 505. If the data used to identify the peak(s) have been stored, then at block 560, these data may be used to reconstruct the current waveform associated with the stimulation therapy as follows: if frequency values are obtained and stored for discrete intervals spanning the entirety of a therapy (e.g., for 1 s for the pulse of FIG. 4A or for the duration of a sine wave of stimulation), then the values can be read out and used to reconstruct the current waveform. If frequency values are obtained and stored for discrete intervals covering only a portion of a therapy, then those values can be read out and used to reconstruct part of the current waveform.

Figure 9:
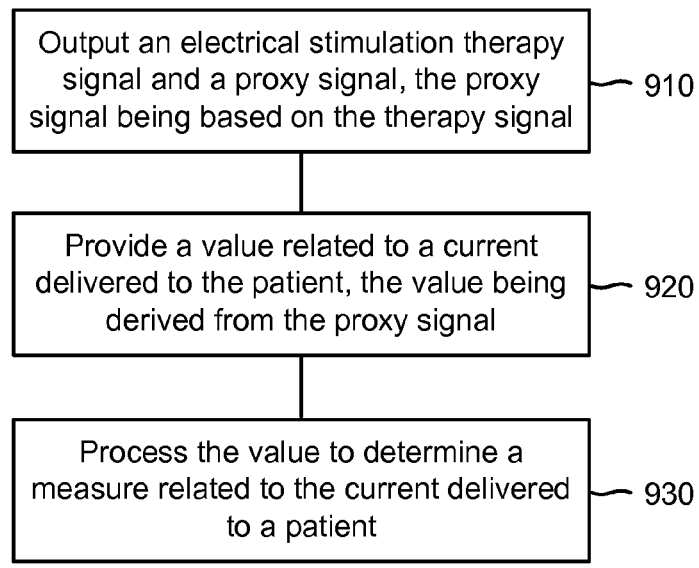
FIG. 9 is a flow chart of a method of acquiring data associated with the current delivered to a patient by an active implantable medical device.

FIG. 9 is a flow chart of a method of acquiring data associated with the current delivered to a patient by an active implantable medical device. The method may be performed by the active implantable medical device. At step 910, the device outputs an electrical stimulation therapy signal and a proxy signal. The proxy signal is based on the therapy signal, and may be proportionate to the therapy signal or a fraction of the therapy signal. The therapy signal and proxy signal may be output by, for example, device circuitry such as the therapy regulator 503 in FIGS. 5 and 6.

At step 920, the device provides a value related to a current delivered to the patient. The value is derived from the proxy signal. The value may be provided by, for example, device circuitry such as the current controlled oscillator 605 in FIG. 6 in combination with one or more of the phase counter 620 and the peak counter 630. For example, the current controlled oscillator 605 may output logic pulses as a function of current amplitude, and the phase counter 620 may output as the value a count corresponding to the number of logic pulses output by the oscillator over a period of time. The period of time may correspond to one of a plurality of phases of the therapy signal. As another example, the current controlled oscillator 605 may output pulses as a function of current amplitude, and the peak counter 630 may monitor for each of a plurality of time windows within one of a plurality of phases of the therapy signal, a count corresponding to the number of output pulses output by the oscillator during the time window. The peak counter 630 may further output as the value the highest count of the plurality of counts.

At step 930, the device processes the value to determine a measure related to the current delivered to the patient. The processing may be provided by, for example, the CPU 328 of FIG. 3. When the value is provided by the phase counter 620, the measure derived by the processor is a total charge. When the value is provided by the peak counter 630, the measure derived by the processor is a peak current delivered to the patient.

Figure 10:
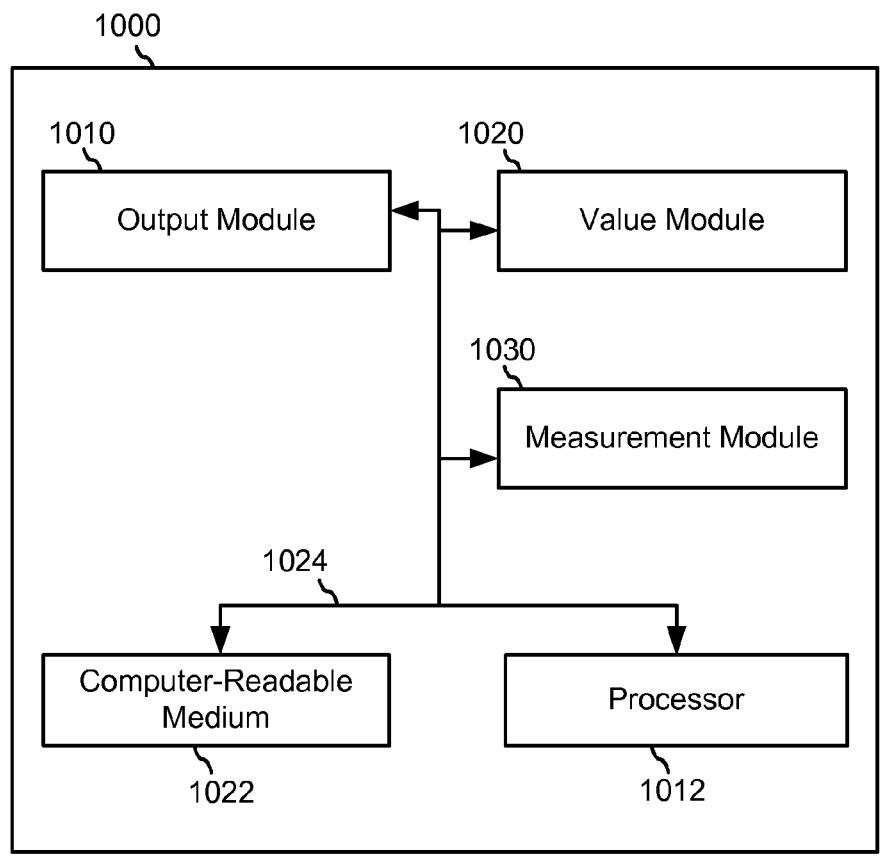
FIG. 10 illustrates a processing system that implements the method of FIG. 9.

FIG. 10 is a diagram illustrating an example of a hardware implementation for an active implantable medical device employing a processing system 1000. The processing system 1000 may be implemented with a bus architecture, represented generally by the bus 1024. The bus 1024 links together various circuits including one or more processors and/or hardware modules, represented by a processor 1012, an output module 1010, a value module 1020, a measurement module 1030, and a computer-readable medium/memory 1022. The processor 1012 may correspond to the CPU 328 of FIG. 3.

The output module 1010 outputs an electrical stimulation therapy signal and a proxy signal, the value module 1020 provides a value related to the current delivered to the patient, and the measurement module 1030 that processes the value to determine a measure related to a current delivered to the patient. These modules may include circuitry described above. For example, the output module 1010 may include the therapy regulator 503 of FIGS. 5 and 6. The value module 1020 may include the current controlled oscillator of FIG. 6 and one or both of the phase counter 620 and the peak counter 630. The measurement module 1030 may include the CPU 328 of FIG. 3.

The processor 1012 is responsible for general processing, including the execution of software stored on the computer-readable medium/memory 1022. The software, when executed by the processor 1012, causes the processing system 1000, including the output module 1010, the value module 1020, and the measurement module 1030, to perform the various functions described above with respect to FIGS. 3, 5, 6, 8 and 9.

Embodiments for measuring data about the current delivered to a patient during a voltage-regulated electrical stimulation therapy may be implemented in an implantable neurostimulation system such as a responsive neurostimulation systems manufacturing by NeuroPace, Inc. under the trade name RNS SYSTEM. A neurostimulation system may include implantable and external components and may be provided with surgical accessories such as a burr hole cover and tools to aid in implanting the implantable components.

The implantable components may include a neurostimulator that is configured to generate one or more different types of neuromodulation signals and deliver the signals to a patient. The neuromodulation signals may include voltage-regulated electrical stimulation, current-regulated electrical stimulation, drug therapy or ultrasonic therapy or the like. The implantable components may also include one or more leads (such as brain leads) that are provided with a plurality of electrodes at a distal end thereof. The electrodes may be configured with a conductive housing of the neurostimulator or with each other to create pathways for current delivered to a patient during a stimulation therapy.

The neurostimulator may be configured to deliver stimulation therapy according to a programmed set of parameters which govern such things as the type of stimulation, the strength of the stimulation, the duration of the stimulation, the conditions under which the stimulation is delivered or triggered, and the shape of the stimulation waveform that is generated and delivered.

A system may be configured so that one or more external components can selectively communicate with the implanted neurostimulator wirelessly, such as via a form of telemetry. Once a communications link is established between the implanted neurostimulator and an external component, the external component may be able to receive data from the implant and/or transfer data to the implant. For example, an external component configured as a patient remote monitor may be enabled only for one-way communication with the implant, so that the patient can use the remote monitor to download data from the implant. On the other hand, an external component configured as a "programmer" may be used by a physician not only to download data from the implant, but also to program or re-program the implant with, for example, parameters that govern the form(s) of stimulation therapy the implanted neurostimulator will generate and under what circumstances, as well as, for example and with reference to the embodiments described herein, how often data should be acquired for current measurements during voltage-regulated stimulation therapy.

The neurostimulation system also may be configured to allow a user to communicate with a central database containing, for example, information previously acquired from the patient's implant, using the programmer or a secure website. The database may include data acquired from or otherwise concerning multiple implanted neurostimulation systems, such as demographic data about patient populations and the like. Neurostimulation systems such as described here are further described in, for example, U.S. Pat. No. 6,690,974 to Archer et al.

It should be appreciated that in embodiments where data about the delivered current are acquired in order to construct a waveform corresponding to the therapy output 505 actually delivered to the patient 540, it may be useful to store other information about the therapy output 505 besides the total charge (integrated current), peak current, and time window values. For example, information about the morphology of the therapy signal 505 might be helpful in constructing a waveform approximating the current delivered to the patient (such as whether the therapy output 505 was a square wave or series of square waves or a different shape, such as a sine wave).

It further should be appreciated that embodiments described here can include multiple configurations for measuring the therapy output 505 delivered during a given electrical stimulation therapy. For example, if the therapy regulator 503 is configured to output more than one therapy output 505 for different stimulation pathways, each stimulation pathway may be associated with a circuit for measuring the current actually delivered to the patient in that pathway. In some embodiments in which the active implantable medical device is configurable to deliver an electrical stimulation therapy signal through from between 9 and 18 electrodes, a circuit such as the circuit described above might be provided and dedicated to each of however many stimulation pathways as might be formed using the available electrodes and the implantable neurostimulator housing. In still other embodiments in which the active implantable medical device is configurable to deliver electrical stimulation therapy signals through multiple pathways, a current measuring circuit may be provided that can be shared by one or more of the pathways and used to measure current or acquire the data to construct a waveform only when a pathway is actually being used to deliver stimulation.

Knowledge of the current being delivered during voltage-regulated stimulation may be used beneficially in various ways that will be apparent to one skilled in the art. For example, if the actual current the patient is experiencing is higher than the current the programmer (i.e., the patient's treating physician) of the implantable neurostimulator would expect the patient to experience based on the programmed settings for the implantable neurostimulator (which may assume an impedance for each therapy output 505), then the power supply for the active implantable medical device (e.g., a primary cell battery) may be used up more quickly than otherwise predicted as therapy continues to be delivered. Conversely, if the actual current the patient is experiencing is less than that expected by the programmer/user, then the power source for the active implantable medical device (e.g., a primary cell battery provided in the implanted device) may be used up more slowly than otherwise predicted as that therapy continues to be delivered. In this case, there would be room for the patient's physician to increase the therapy to the patient therapy if deemed appropriate. Thus, information about the amount of current delivered at a given constant voltage may be used by the active implantable medical device to adjust estimates of the remaining useful life of its battery.

Additionally, knowledge of the current actually delivered during a given therapy may be used to adjust one or more parameters (automatically or otherwise), for example, with the goal of delivering electrical stimulation therapy that is more charge balanced or that otherwise more closely approximates what the physician intended the patient to receive at the time he or she programmed the electrical current stimulation therapy signal.

Example embodiments for estimating the current delivered to a patient during a therapy of electrical stimulation generated using a controlled voltage are thus described. While the present technology has been described in particular examples, it should be appreciated that the present technology should not be construed as limited by such examples, but rather construed according to the claims.

In one embodiment, a method for acquiring data associated with the current delivered to a patient during a voltage-regulated electrical stimulation therapy generated by an active implantable medical device, includes using circuitry and memory under the control of a processor in the active implantable medical device to: create a signal comprising a proxy for the current being delivered to the patient; generate a signal proportionate to the current being delivered to the patient; count the logic pulses to calculate a total charge delivered for the therapy; evaluate the logic pulses to identify at least one peak current occurring during the therapy; evaluate the logic pulses to identify at least one time window corresponding to each peak current; and store values associated with the total charge calculation, each at least one peak current and each at least one time window. The circuitry to create the current proxy signal may include a current mirror circuit. The circuitry to generate the signal proportionate to the current proxy signal may include a current controlled oscillator.

In another embodiment, a system for estimating an amount of current delivered to a patient during a therapy of electrical stimulation generated using a regulated voltage includes an implantable neurostimulator programmable to deliver at least one electrical stimulation therapy signal to a patient, wherein the at least one electrical stimulation therapy signal comprises a pulse characterized by at least one phase. The implantable neurostimulator includes a current measuring subsystem configured to generate a mirrored current signal, wherein the mirrored current signal comprises a percentage of the at least one electrical stimulation therapy signal that is delivered to the patient wherein the mirrored current signal mirrors the at least one electrical stimulation therapy signal; a circuit coupled with the current measuring subsystem, the circuit configured to generate a plurality of logic pulses corresponding to the mirrored current signal and characterized by a frequency; at least one phase counter coupled with the output of the logic pulse generating circuit, the at least one phase counter configured to count the logic pulses output wherein the count is a function of a total charge delivered to the patient in each phase of the at least one phase; at least one peak current counter coupled with the output of the logic pulse generating circuit, the at least one peak current counter configured to determine at least one peak current and a corresponding time window in which the at least one peak current occurred for the each phase of the at least one phase can be estimated; and at least one memory module coupled with any of the at least one phase counter and the at least one peak current counter, the at least one memory module configured to store a set of values corresponding to each phase of the at least one phase, the set of values representing at least the total charge delivered to the patient in each phase of the at least one phase and the peak current delivered to the patient during each phase of the at least one phase. The system may further include a pulse reconstruction module coupled with the implantable neurostimulator, the pulse reconstruction module configured for reconstructing a set of waveforms associated with the electrical stimulation therapy signal delivered to the patient, the pulse reconstruction module using information stored in the at least one memory module.

It should be noted that there can be a variety of ways in which systems and methods according to embodiments may be implemented. For example, software, hardware (including ASICs, FPGAs, and other custom electronics), and various combinations of software and hardware, are all solutions that would be possible to practitioners of ordinary skill in the art of electronics and systems design. It should further be noted that the methods described herein may be performed in software and/or hardware: hardware may be preferable in some instances to reduce computational load on the processor of the active implantable medical device. Various embodiments may be carried out by processors and electrical components under the control of computer readable and computer executable instructions. The computer readable and computer executable instructions reside, for example, in a non-transitory data storage medium such as computer usable volatile and non-volatile memory. However, the computer readable and computer executable instructions may reside in any type of non-transitory computer readable storage medium.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

The invention claimed is:

1. An active implantable medical device comprising:
a therapy regulator configured to output an electrical stimulation therapy signal for delivery to a patient, and a proxy signal, the therapy signal resulting in delivery of a current to the patient, and the proxy signal being characterized by a current waveform that is based on the current delivered to the patient;
circuitry configured to derive a value related to the current delivered to the patient, the value being derived from the current waveform of the proxy signal; and
a processor configured to process the value to determine a measure related to the current delivered to the patient,
wherein the therapy signal comprises a pulse having a plurality of phases, at least one of the plurality of phases having a plurality of time windows, and the circuitry comprises:
an oscillator configured to output pulses as a function of an amplitude of the current waveform; and
a peak counter configured to monitor for each of the plurality of time windows within one of the plurality of phases, a count corresponding to the number of output pulses output by the oscillator during the time window, and to output as the value the highest count of the plurality of counts.

2. The device of claim 1, wherein the proxy signal is proportionate to the therapy signal.

3. The device of claim 1, wherein the proxy signal is a fraction of the therapy signal.

4. The device of claim 1, wherein:
the circuitry further comprises a phase counter configured to output as a second value a count corresponding to the number of output pulses output by the oscillator over a period of time corresponding to one of the plurality of phases; and
the processor is further configured to process the second value to determine a second measure related to the current delivered to the patient.

5. The device of claim 4, wherein the second measure comprises a total charge.

6. The device of claim 1, wherein the measure comprises a peak current delivered to the patient.

7. The device of claim 1, wherein the processor is configured to determine the measure at least one of: every time a therapy signal is output, periodically as a function of a number of therapy signals output, and as a function of time.

8. A method of acquiring data associated with the current delivered to a patient by an active implantable medical device, the method comprising:
outputting an electrical stimulation therapy signal for delivery to a patient, and a proxy signal, the therapy signal resulting in delivery of a current to the patient, and the proxy signal being characterized by a current waveform that is based on the current delivered to the patient;
deriving a value related to the current delivered to the patient, the value being derived from the current waveform of the proxy signal; and
processing the value to determine a measure related to the current delivered to the patient,
wherein the therapy signal comprises a pulse having a plurality of phases, at least one of the plurality of phases having a plurality of time windows, and deriving a value comprises:
using an oscillator to output pulses as a function of an amplitude of the current waveform;
monitoring for each of the plurality of time windows within one of the plurality of phases, a count corresponding to the number of output pulses output by the oscillator during the time window; and
outputting as the value the highest count of the plurality of counts.

9. The method of claim 8, wherein the proxy signal is proportionate to the therapy signal.

10. The method of claim 8, wherein the proxy signal is a fraction of the therapy signal.

11. The method of claim 8, wherein:
deriving a value further comprises outputting as a second value a count corresponding to the number of output pulses output by the oscillator over a period of time corresponding to one of the plurality of phases; and
further comprising processing the second value to determine a second measure related to the current delivered to the patient.

12. The method of claim 11, wherein the second measure comprises a total charge.

13. The method of claim 8, wherein the measure comprises a peak current delivered to the patient.

14. The method of claim 8, wherein processing the value to determine the measure occurs at least one of: every time a therapy signal is output, periodically as a function of a number of therapy signals output, and as a function of time.

15. A method for acquiring data associated with a current delivered to a patient during a voltage-regulated electrical stimulation therapy generated by an active implantable medical device, the method comprising:

delivering the current to the patient;

creating a current proxy signal based on the current being delivered to the patient;

generating a proportionate signal comprising a plurality of logic pulses, wherein a rate of the plurality of logic pulses is proportionate to a current of the current proxy signal;

counting the logic pulses in the proportionate signal to calculate a total charge delivered to the patient;

creating a plurality of discrete time windows during the therapy;

counting the logic pulses in the proportionate signal as a function of the plurality of discrete time windows;

identifying at least one peak current occurring during the therapy and a discrete time window within which the at least one peak current occurred; and storing values associated with the total charge calculation, each at least one peak current, and each at least one discrete time window within which the at least one peak current occurred.

16. The method of claim 15 wherein the circuitry to create the current proxy signal includes a current mirror circuit.

17. The method of claim 15 wherein the circuitry to generate the proportionate signal includes a current controlled oscillator.

\* \* \* \* \*